US006042673A

United States Patent [19]

Johnson et al.

[11] Patent Number: 6,042,673

[45] Date of Patent: Mar. 28, 2000

[54] METHOD FOR MAKING A FLANGELESS SEAM FOR USE IN DISPOSABLE ARTICLES

[75] Inventors: Larry Kenneth Johnson; Stephen Joseph Lange, both of Cincinnati, Ohio

[73] Assignee: The Procter & Gamble Company, Cincinnati, Ohio

[21] Appl. No.: 09/034,763

[22] Filed: Mar. 4, 1998

Related U.S. Application Data

[63] Continuation-in-part of application No. 08/855,651, May 15, 1997.

[51] Int. Cl.$^{7}$ .......... B32B 31/24

[52] U.S. Cl. .......... 156/227; 156/272.4; 156/274.8; 156/275.3; 156/286; 604/385.1

[58] Field of Search .......... 156/73.4, 163, 156/164, 217, 227, 272.4, 273.7, 273.9, 274.4, 274.8, 275.1, 275.3, 275.7, 289, 308.4; 219/633, 634; 604/365, 366, 385.1, 385.2, 386, 392; 2/402

[56] References Cited

U.S. PATENT DOCUMENTS

| | | | |
|---|---|---|---|
| 1,602,689 | 10/1926 | Lissner . | |
| 2,115,368 | 4/1938 | Lustberg | 112/262 |
| 2,298,522 | 10/1942 | Waters | 93/35 |
| 2,372,632 | 3/1945 | Webb et al. | 154/42 |
| 2,393,541 | 1/1946 | Kohler | 156/272.4 |
| 2,494,905 | 1/1950 | Shumann | 93/35 |
| 3,574,031 | 4/1971 | Heller et al. | 156/272.4 |
| 4,205,679 | 6/1980 | Repke et al. | 128/287 |
| 4,610,681 | 9/1986 | Strohbeen et al. | 604/396 |
| 4,731,070 | 3/1988 | Koci | 604/385 R |
| 4,890,763 | 1/1990 | Curiel | 220/455 |
| 4,938,753 | 7/1990 | Van Gompel et al. | 604/385.2 |
| 5,185,052 | 2/1993 | Chappell et al. | 156/462 |
| 5,236,430 | 8/1993 | Bridges | 604/396 |
| 5,246,433 | 9/1993 | Hasse et al. | 604/396 |
| 5,491,846 | 2/1996 | Muller | 2/400 |
| 5,569,234 | 10/1996 | Buell et al. | 604/396 |
| 5,575,782 | 11/1996 | Hasse et al. | 604/385.1 |
| 5,607,537 | 3/1997 | Johnson et al. | 156/289 |
| 5,618,366 | 4/1997 | Suekane | 156/73.1 |
| 5,622,589 | 4/1997 | Johnson et al. | 156/308.4 |
| 5,662,638 | 9/1997 | Johnson et al. | 604/385.1 |

FOREIGN PATENT DOCUMENTS

WO 98/51252 11/1998 WIPO .

OTHER PUBLICATIONS

Scheel, Mark A., "Induction Heating of Adhesives for Bonding of Thermoplastics and Composites", SAE Technical Paper No. 930332.

"Emaweld" Bulletin1688, Ashland Oil, Inc., Copyright 1987.

Molnar, S.P., "Characterization and Control of Induction Fusion Bonding of Thermoplastic Composite", ANTEC '92, pp. 2102–2105.

Product Bulletin for Ameritherm 1kW and 3kW Radio Frequency Induction Heating Power Supplies, Ameritherm, Inc., Scottsville, NY.

*Primary Examiner*—Michael W. Ball
*Assistant Examiner*—Michael A Tolin
*Attorney, Agent, or Firm*—David M. Weirich; Steven W. Miller; Jacobus C. Rasser

[57] ABSTRACT

A method of making a flangeless seam for a disposable article including the following steps: A first member of the disposable article is provided. A conductive member is provided on the first member. The first member is folded about the conductive member providing opposing first proximal and first distal portions of the first member, the conductive member being disposed at least partially between the opposing first proximal and first distal portions. A second member of the disposable article is provided in a folded configuration juxtaposed at least a portion of the first member to form a laminate including the first member and the second member. An electromagnetic field is applied across at least a portion of the laminate to heat the conductive member to a temperature which joins at least a portion of the first member and at least a portion of the second member. The resulting seam can be opened to provide the article with a flangeless seam.

20 Claims, 6 Drawing Sheets

10 46 34 30 30 34 76 20 76 30 30 90 56 90 10 58 14 48 26 24 22 75 57 32

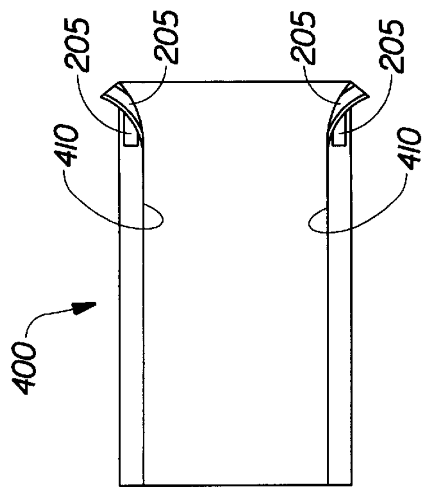
Fig. 5C
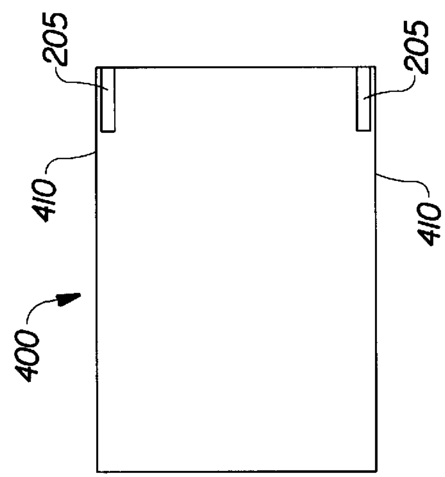
Fig. 5B
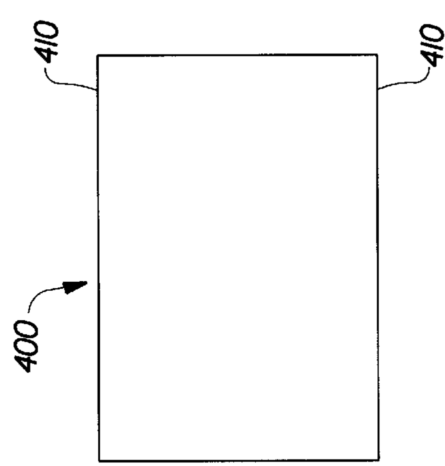
Fig. 5A
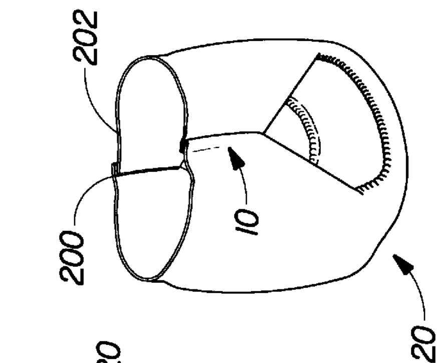
Fig. 5G
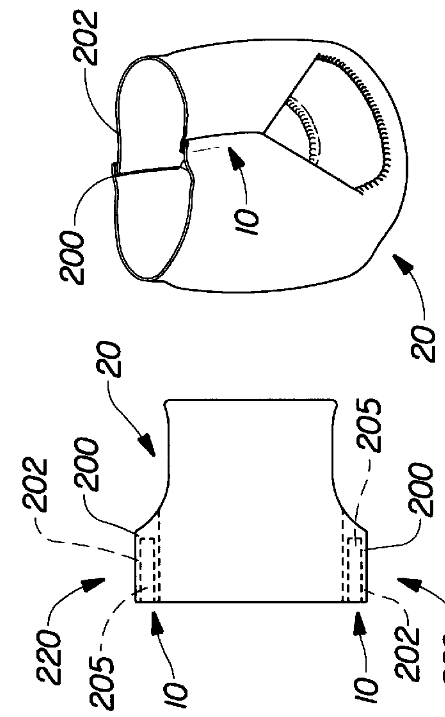
Fig. 5F
Fig. 5E
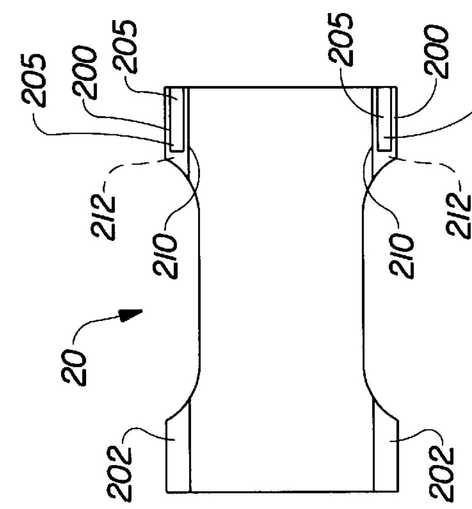
Fig. 5D

METHOD FOR MAKING A FLANGELESS SEAM FOR USE IN DISPOSABLE ARTICLES

This application is a continuation in part of Ser. No. 08/855,651 filed May 15, 1997.

FIELD OF THE INVENTION

The present invention relates to a method for making flangeless seams especially preferred for use in disposable, pant-like articles having at least one fixed side comprising a seam. Examples of such disposable articles include training pants, pull-on diapers or adult incontinence articles, disposable underwear for children (e.g., toddlers) or adults, and disposable panties which may be used with catamenial devices such as tampons or sanitary napkins.

BACKGROUND OF THE INVENTION

Infants and other incontinent individuals wear disposable absorbent articles to receive and contain urine and other bodily exudates. Absorbent articles having fixed sides have been popular for use in adult incontinence articles and children's toilet-training articles because it is desirable to have an absorbent article which is very garment-like in appearance and feel. (As used herein, "articles having fixed sides" refer to disposable articles such as adult incontinence briefs and training pants which are provided to the consumer in a pant-like configuration. Thus, the articles generally have the front and rear portions joined together to form a waist hoop and leg holes. This is unlike conventional diapers which are provided to the consumer with the front and rear portions unjoined.) For adults, the garment-like appearance and feel can help reduce any embarrassment associated with the use of incontinence articles. For children, especially in their toilet training stage, the garment-like feel and appearance can help the child distinguish the article, such as training pants, from a diaper and can help the child adjust to cloth undergarments.

One example of a commercially available disposable training pant is disclosed in U.S. Pat. No. 5,246,433 entitled "Elasticized Disposable Training Pant and Method of Making the Same", issued to Hasse et al. on Sep. 21, 1993. Although this training pant has been a commercial success, it still suffers because it includes seams joining the front and rear portions which are not garment-like in appearance. Such seams are often constructed by positioning the lateral edges of the front and rear portions of the article in a face-to-face relationship with one another and then gluing, sewing, heat sealing, pressure bonding or ultrasonically sealing the edges to form flanges or fin seams. The flanges or fins are unsightly if located on the outwardly facing surface of the article or irritating to the wearer if located on the inward surface. Thus, attempts have been made to reduce the outwardly or inwardly extending portions of the flanges of fin seams. However, in so doing the process for making the seams generally becomes more complex and costly and may reduce the strength of the bond.

Thus, it would be advantageous to be able to provide a flangeless seam that can be constructed economically. It would also be advantageous to provide a flangeless seam that could be produces on machinery that is very similar to that already in place. Further, it would be advantageous to reduce the amount of material that is needed to produce an aesthetically pleasing seam that is strong enough to hold together the front and rear portions of a disposable absorbent article.

SUMMARY OF THE INVENTION

The method of then present invention provides a solution to the problems of the prior art by providing an inexpensive means to manufacture flangeless seams. The method includes the following steps: A first member of the disposable article is provided. A conductive member is provided on the first member. The first member is folded about the conductive member providing opposing first proximal and first distal portions of the first member, the conductive member being disposed at least partially between the opposing first proximal and first distal portions. A second member of the disposable article is provided in a folded configuration juxtaposed at least a portion of the first member to form a laminate including the first member and the second member. An electromagnetic field is applied across at least a portion of the laminate to heat the conductive member to a temperature which joins at least a portion of the first member and at least a portion of the second member. The resulting seam can be opened to provide the article with a flangeless seam.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIGS. 5A–G show a schematic view of a portion of one preferred embodiment of the method of the present invention;

DETAILED DESCRIPTION OF THE INVENTION

Figure 1:
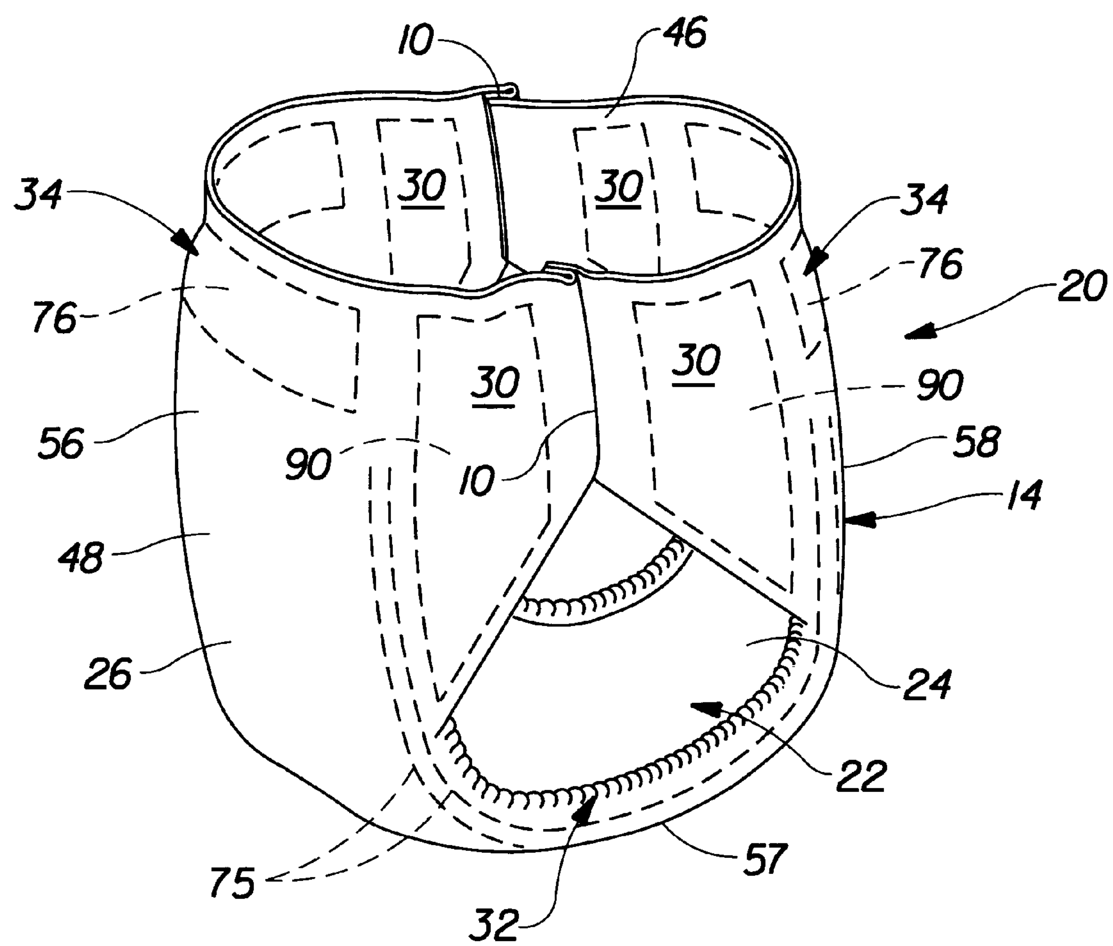
FIG. 1 is a perspective view of one embodiment of a disposal training pant in a typical in-use configuration as it would be applied to a wearer comprising a seam formed by one embodiment of the present invention.

Referring to the drawings, it will be noted that FIG. 1 is a perspective view of a unitary disposable article. A unitary disposable article is one which is intended to be discarded after it is used (i.e., it is generally not intended to be laundered or otherwise restored or reused). The disposable article may be provided with an absorbent assembly which is placed in close proximity to the body of the wearer to absorb and contain the various exudates discharged from the body. A preferred embodiment of the disposable article of the present invention, disposable training pants 20, is shown in FIG. 1.

The training pants 20 of FIG. 1, preferably comprise a chassis 14, an absorbent assembly 22, and at least one flangeless seam 10. (As used herein the term "flangeless seam" refers to a seam which extends from the disposable training pants 20 about ⅛ inch or less. Preferably the flangeless seam 10 will extend from the article about 1/16 inch or less, and more preferably 1/32 inch or less.) The chassis 14 of the present invention preferably has a symmetric, modified hour-glass shape. The chassis 14 preferably comprises a front portion 56, a rear portion 58, a crotch portion 57. The chassis 14 preferably further comprises elasticized leg cuffs 32, an elasticized waistband 34, elasticized side panels 30 and longitudinal side regions 88. The longitudinal side regions 88 preferably comprise a polymeric material to facilitate the seaming process which is described in greater detail below.

The training pants 20 preferably further comprises an absorbent assembly 22 preferably secured to the chassis 14 by any means known in the art. The absorbent assembly preferably comprises a liquid permeable topsheet 24, a liquid impervious backsheet 26 and an absorbent core 28 sandwiched between the topsheet 24 and the backsheet 26.

Figure 2:
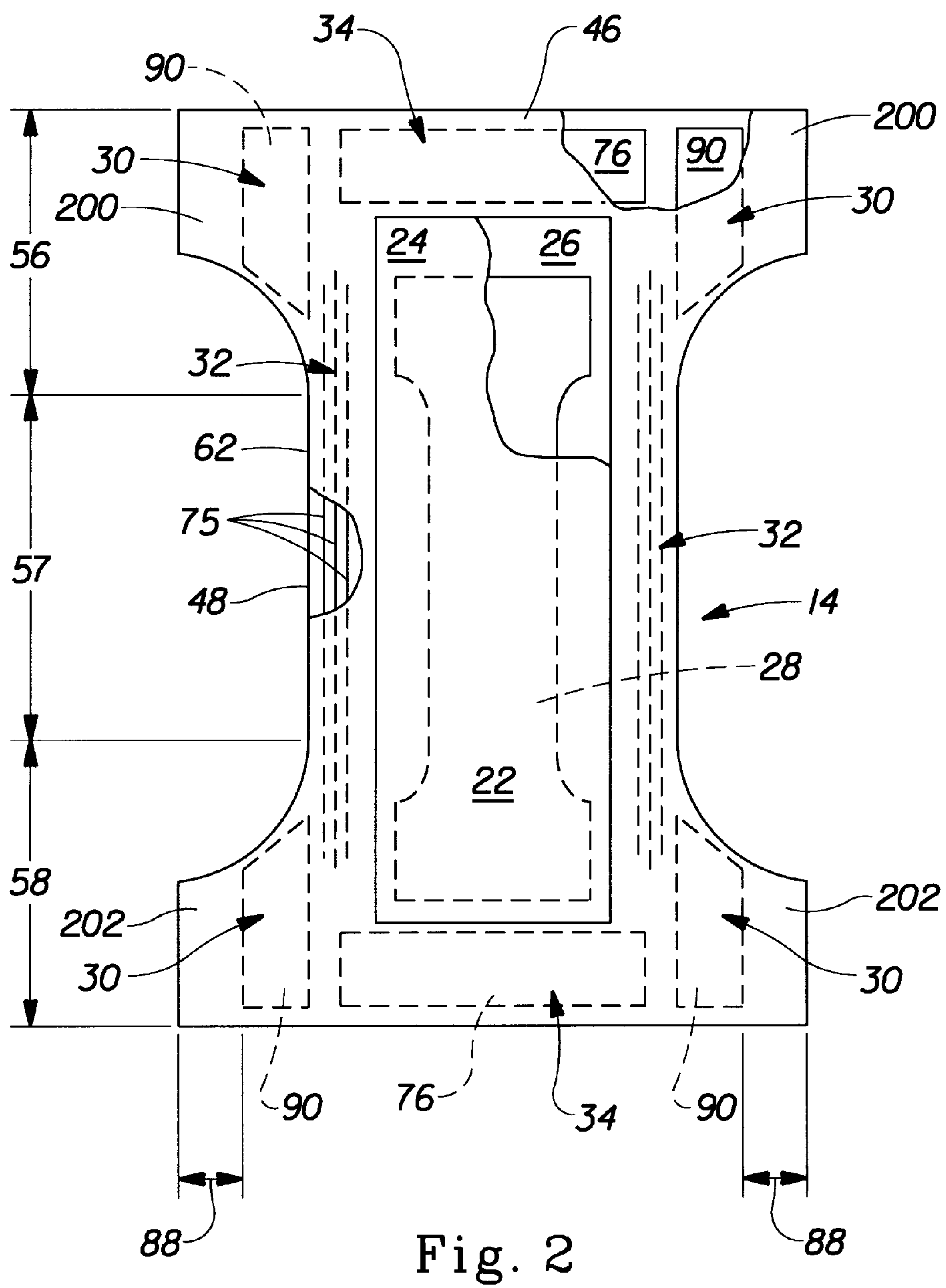
FIG. 2 is a plan view of the chassis of the training pant of FIG. 1 having portions cut away to reveal the underlying structure, the surface which will form the outer surface of the disposable article facing away from the viewer.

FIG. 2 is a partially cut-away perspective view of the disposable article 20 of FIG. 1, prior to the front portion 56 and the rear portion 58 of the chassis 14 being joined together. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.) As shown in FIG. 2, a preferred embodiment of the chassis 14 will comprise an outer cover 48, an inner cover 46, elastic side panel members 90, elastic waistband members 76, and elastic strands 75 secured between the inner cover 46 and the outer covers 48.

The inner cover 46 is that portion of the chassis 14 which will form the interior of the disposable training pants 20. The outer cover 48 is that portion of the chassis 14 which will form the exterior of the disposable training pants 20, i.e. face away from the wearer. The outer cover 48 is preferably liquid impervious or hydrophobic, yet breathable or pervious to vapors. The inner cover 46 and the outer cover 48 are preferably compliant, soft feeling, and non-irritating to the wearer's skin. A suitable inner or outer cover may be manufactured from a wide range of materials, such as plastic films including microporous films; woven or non-woven webs of natural fibers (e.g. wood or cotton fibers), synthetic fibers (e.g. polyester or polypropylene fibers), a combination of natural and synthetic fibers, or laminates of any of these or other known materials. Preferably, the inner and outer covers 46 and 48 comprise a significant amount of thermoplastic fibers, typically 50% or more, preferably 100%. Material suitable for use as an inner or outer cover is Series 6700 Nonwoven manufactured by PGI Nonwovens of Landisville, N.J.

In a preferred embodiment of the present invention, at least a portion of the inner and outer covers 46, 48 will be subjected to mechanical stretching in order to provide a "zero strain" stretch laminate that forms the elasticized side panels 30. Thus, the inner and outer covers 46, 48 are preferably elongatable, most preferably drawable, but not necessarily elastomeric, so that the inner and outer covers 46, 48 will, upon mechanical stretching, be at least to a degree permanently elongated such that they will not fully return to their original undistorted configuration. In preferred embodiments, the inner and outer covers 46, 48 can be subjected to mechanical stretching without undue rupturing or tearing. Thus, it is preferred that the inner and outer covers 46, have a low cross-machine direction (lateral direction) yield strength.

Suitable "zero strain" stretch laminates and methods for producing them are disclosed in U.S. Pat. No. 5,330,458 entitled "Absorbent Article With Elastic Feature Having A Portion Mechanically Prestrained" issued to Buell et al., on Jul. 19, 1994; U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the inner and outer covers 46, 48 or portions thereof may comprise a structural elastic-like film (SELF) web. A structural elastic-like film web is an extensible material that exhibits an elastic-like behavior in the direction of elongation without the use of added elastic materials. SELF webs suitable for the present invention are more completely described in the co-pending, commonly assigned U.S. Pat. No. 5,554,145, in the name of Donald C. Roe, et al., entitled "Absorbent Article with Multiple Zone Structural Elastic-Like Film Web Extensible Waist Feature" issued Sep. 10, 1996; and U.S. Pat. No. 5,518,801 , in the names of Chappell, et al, entitled "Web Materials Exhibiting Elastic-Like Behavior" issued May 21, 1996, both of which are incorporated herein by reference.

A more detailed description of a suitable training pant, as well as preferred components and alternative embodiments, in which the method and seams of the present invention may be used can be found in U.S. Pat. No. 5,236,430 entitled "Disposable Training Pant Having Fusion-Slit Side Seams", issued to Russell P. Bridges on Aug. 17, 1993, and U.S. Pat. No. 5,246,433 entitled "Elasticized Disposable Training Pant and Method of Making the Same", issued to Hasse et al. on Sep. 21, 1993. The specification, claims and drawings of each of these patents are hereby incorporated by reference herein.

Method of Making a Flangeless Seam

One preferred method for making flangeless seams especially useful in disposable articles, such as training pants, incontinence articles and the like is shown schematically in FIGS. 5A–5G. The step depicted in FIG. 5A shows providing a web 400 having longitudinal side edges 410 that will be processed into disposable article 20 having first members 200 and second members 202 to be joined. FIG. 5B shows conductive member 205 provided juxtaposed at least a portion of each longitudinal side edge 410. FIG. 5C shows the longitudinal side edges 410 being folded over the web 400. A second conductive member 205, as shown in FIG. 5C, may be provided adjacent the folded over longitudinal side edges 410. FIG. 5D shows the chassis 14 of the disposable article 20 with the side notches 10 removed.

Figure 3:
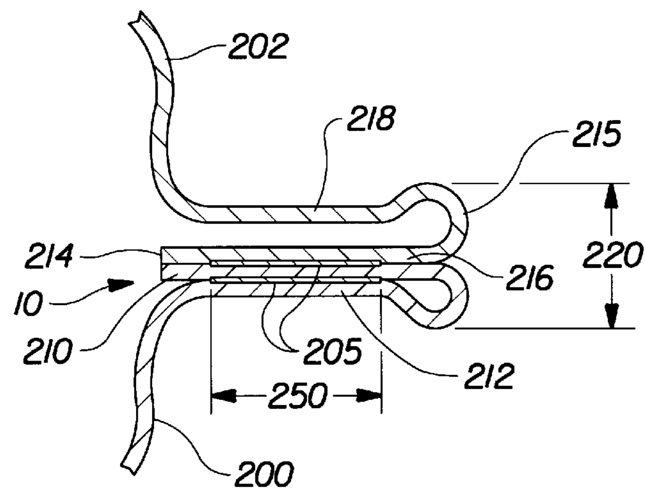
FIG. 3 is an enlarged cross-sectional view of one embodiment of a seam made by one embodiment of the present invention in the configuration in which portions of the seam are joined together.

First member 200 is preferably folded about the conductive member 205 providing opposing first proximal and first distal portions 210 and 212. The conductive member 205 is preferably disposed at least partially between the opposing first proximal and first distal portions 210 and 212. (The “proximal portion” is that portion of the first or second member which is joined, or will be joined, either directly or indirectly, to a portion of the disposable article 20, preferably other than the second member 202. The “distal portion” is that portion of the first member 200 or second member 202 extending from the proximal portion to the comprising the free end 214.) FIG. 5E shows the second member 202 of the disposable article 20 being provided juxtaposed at least a portion of the first member 200 forming a laminate 220 of the first member 200, the second member 202 and the conductive member(s) 205. (A more detailed drawing of the laminate 220 is shown in FIG. 3.) Other embodiments, however, are contemplated wherein the conductive member 205 is disposed in a location other than between the first proximal and distal portion. For example, the conductive member 205 may be disposed between the proximal portion of the first member 200 and the distal portion of the second member 202, between the distal portion of the first member 200 and the proximal portion of the second member 202 or any other locations suitable for joining the first and second members.

Figure 6:
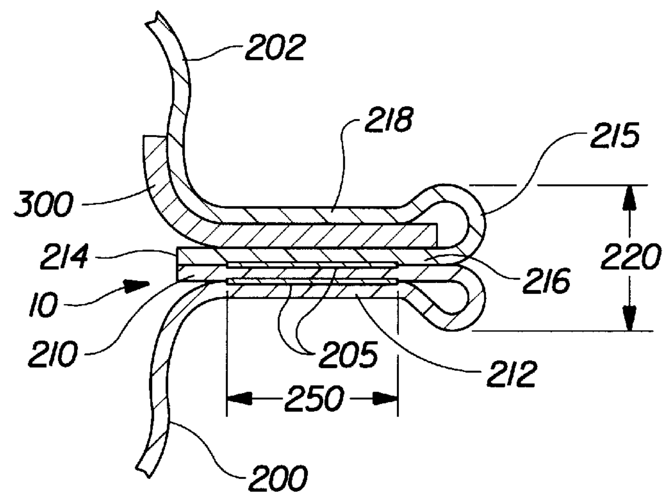
FIG. 6 is an enlarged cross-sectional view of one embodiment of a seam made by one embodiment of the present invention in the configuration in which portions of the seam are joined together.
Figure 7:
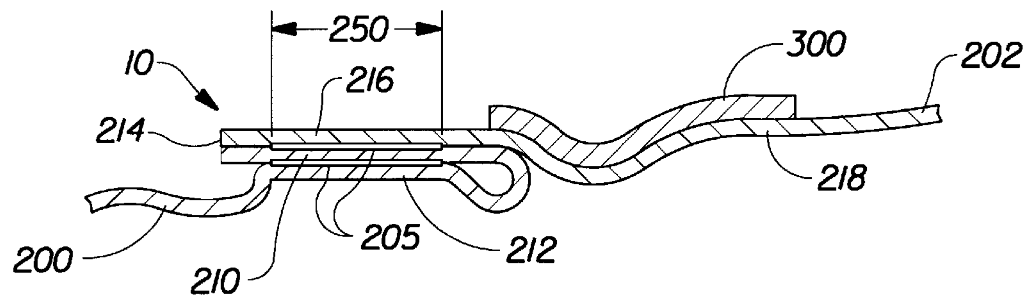
FIG. 7 is an enlarged cross-sectional view of the seam area shown in FIG. 3 in an open configuration.
Figure 8:
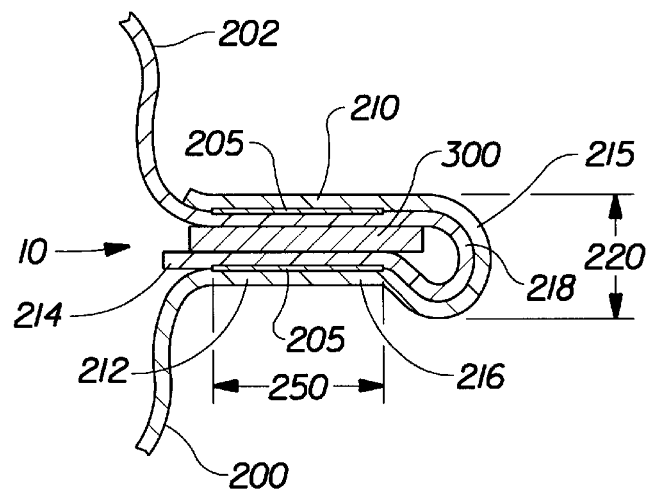
FIG. 8 an enlarged cross-sectional view of one embodiment of a seam made by one embodiment of the present invention in the configuration in which portions of the seam are joined together.

FIG. 5F shows the diaper 20 in a configuration for seaming laminate 220. An electromagnetic field is provided across the seam area 250, heating the conductive member(s) 205 and joining at least a portion of the first member 200 and the second member 202 to form seam 10. The duration of the electromagnetic field and/or the conductive member(s) 205 may be varied such that opposing second proximal and second distal portions 216 and 218 remain unjoined to each other. Alternatively, as shown in FIGS. 6–8, a barrier member 300 may be used to prevent the joining of the opposing second proximal and second distal portions 216 and 218. Thus, the seam 10 may be opened from the configuration in which it is sealed (one embodiment is shown in FIG. 3) to a flangeless configuration wherein opposing second proximal and second distal portions 216 and 218 of the second member 202 are in a relatively planar configuration with regard to one another. (An example of the seam in a planar configuration is shown in FIG. 5G and in more detail in FIG. 3A).

It should be noted that the scope of the present invention is not intended to be limited by the particular order in which the steps of the method are described. For example, although the side notches 10 are shown to be removed first in FIG. 5D, it is contemplated that the side notches 10 may be removed before, after or during any other step of the process. Further, the method of the present invention can be performed on-line in conjunction with, or at separate time and/or in a location remote from, the manufacture of the absorbent article which comprise the seams formed by the present method. If the process is performed on-line in conjunction with the manufacture of the absorbent article, the seams may be formed before, after or at the same time that the first and second members 200 and 202 are joined with the chassis 14 of the disposable article 20. Also, it should be understood that the exact size and shape of any member comprised in the disposable article 20, as well as the materials comprised in the members may vary depending on the desired characteristics of the disposable article 20.

As described above, the method for manufacturing a flangeless seam preferably includes providing a first member 200 and a second member 202. The chassis 14 preferably comprises at least one longitudinal side region 88 having a first member 200 and a second member 202. As shown in FIG. 2, the chassis 14 more preferably comprises a pair of opposing longitudinal side regions 88, each of which comprise a first member 200 and a second member 202. (Although the first members 200 are shown in FIG. 2 to be disposed in the front portion 56 and the second members 202 are shown to be disposed in the rear portion 58, embodiments are contemplated wherein the first members 200 are disposed in the rear portion 58 and the second members 202 are disposed in the front portion 56.)

The first and second members 200 and 202 may be separate members joined to the longitudinal side regions 88 or may be integral with the longitudinal side regions 88. (As used herein, the term “integral” refers to elements that are joined to one another in such a way that the elements are neither divided nor discontinuous with the other elements.) If the first and second members 200 and 202 are joined with the chassis 14, any suitable means for joining known in the art may be used. In a preferred embodiment, the first and second members 200 and 202 are extensions of the topsheet 24, the backsheet 26, both the topsheet 24 and the backsheet 26 or any other element or elements of the disposable article that may be suitable for joining to form a seam 10.

The first member 200 and the second member 202 may comprise any material known in the art that is suitable for use in disposable articles such as training pants 20 which may be joined together to form seam 10. Examples of suitable materials include, but are not limited to polymeric films, woven webs, nonwoven webs or combinations of these or other suitable materials known in the art. Examples of preferred materials include the carded nonwoven DPN290 available from Fiberweb, Clopay 1401 polyethylene film available from the Clopay Corporation of Cincinnati, Ohio, and FS2 or Plus polyethylene films available from Tredegar Film Products, Inc., of Terre Haute Ind.

The method of the present invention further comprises the step of providing one or more conductive members 205, as shown in FIGS. 5B and 5C. The conductive member(s) 205 heat up when an electromagnetic field is provided, thereby melting and joining at least a portion of the first member 200 and the second member 202. (It is believed the conductive member 205 becomes heated because of Joule heating or the decay of a current induced in the conductive member 205 by the external magnetic field. However, Applicants do not wish to be limited to this theory.) Alternatively, the conductive member 205 may heat up a substance added to or coated on either the first member 200, the second member 202 or the conductive member 205. In such cases, the added material or member becomes active adhesively, cohesively or the like to join the first member 200 and the second member 202. Examples of suitable substances to be added to the seam area are hot melt adhesives which can be obtained from Ato Findley Adhesives, Inc. of Wauwatosa, Wis. as H-2120 or H-2379.

The conductive member(s) 205 may include any conductive material or materials and may take on any shape, size or configuration suitable for the particular seam to be formed. Further, the conductive member(s) 205 may be separate elements joined to the first or second member(s) 200 and 202 or a separate member not joined to the first or second members 200 and 202, but merely provided in a position to react to the electromagnetic field while the seam 10 is being formed. Alternatively, the conductive member(s) 205 may comprise an element or material that is unitary or integrated with at least a portion of the first member 200 or second member 202, such as a material coextruded with the first member 200 or the second member 202, or portion of the first member 200 or second member 202 that has been coated or impregnated to act as a conductive member.

Examples of suitable conductive members 205 include, but are not limited to ferro-magnetic materials, metallic foils and screens such as aluminum, copper and nickel, metallic powders such as bismuth powder and any conductive materials known in the art. (As used herein the term "conductive" refers to materials which increase in temperature when in the presence of eddy currents generated by an alternating current flowing through an electromagnetic coil.) The conductive members 205 may also be in the form of a composite material such as a solution, adhesive, lotion, film, web, etc. including the conductive material. Some exemplary conductive materials are available from the Ashland Chemical Company under the trade name EMAWELD. Generally, the composition of the conductive members 205 will be limited only by the particular electromagnetic frequency to be used and intensity of heat which is needed to properly join the first member 200 and the second member 202. The conductive material may also be magnetic which may increase the efficiency of the heating due to an hysteric loss of the material when it is placed in an electromagnetic field.

The means by which the conductive member 205 may be provided, as well the timing and location for providing the conductive member 205 win be dependent on the exact conductive member 205 chosen. However, once a particular conductive member 205 has been chosen, the conductive member 205 may be provided by any suitable means known in the art. For instance, if a conductive member 205 comprising bismuth powder is chosen, one preferred means for providing the barrier member 205 is spraying the bismuth powder composition onto at least a portion of the first member 200. If the conductive member is a metallic foil, the foil may be cut and slipped into place in the seam region 250 at any point in the process before the seam is made. The conductive member 205 may be removed from the seam area 250 once the seam 10 is made or may remain as part of the finished seam 10.

Figure 4:
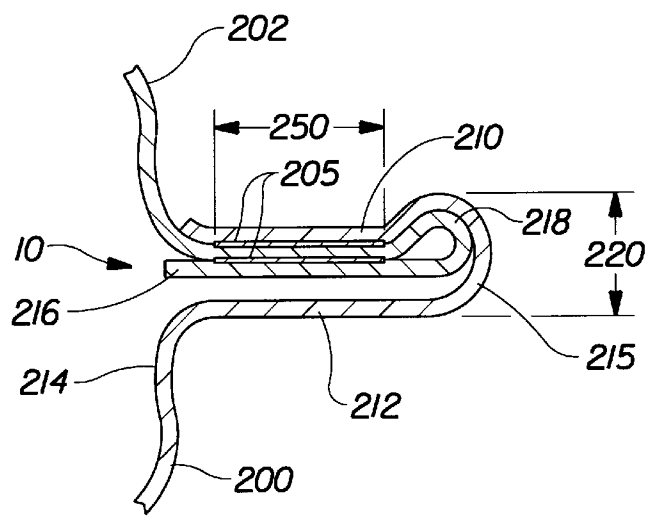
FIG. 4 is an enlarged cross-sectional view of one embodiment of a seam made by one embodiment of the present invention in the configuration in which portions of the seam are joined together.

In one preferred embodiment, as shown in FIG. 3, once the conductive member 205 is provided, the first member 200 is folded about the conductive member 205. (As stated above, the exact order of the steps of the process are not critical, thus, the conductive member 205 may be provided before or after the first member 200 is folded.) The fold 215 preferably separates the first member 200 into two portions, a first proximal portion 210 and an opposing first distal portion 212. Preferably, the conductive member 205 is disposed at least partially between the opposing first proximal and first distal portions 210 and 212, as shown in FIG. 3. The length of the first proximal portion 210 and the first distal portion 212 is not critical, and either or both may comprise any number of layers and/or folds. In fact, it is recognized that one way to increase the strength of the finished seam is to provide more material in the seam area 250. In an alternative embodiment, the first member 200 is folded about the conductive member 205 and at least a portion of the second member 202, as shown in FIG. 4.

The method of the present invention further comprises the step of providing a second member 202 having a second proximal portion 218 and a second distal portion 216. The second member 202 is preferably provided juxtaposed at least a portion of the first distal portion 210 of the first member 200 at a location wherein the opposing first proximal and first distal portions 210 and 212 have the conductive member 205 disposed between them. This forms a laminate 220 (one embodiment of which is shown in FIG. 3) including the first member 200, the second member 202 and the conductive member 205. (As used herein, the term "laminate" refers to any number of materials that are in a generally overlapping configuration so as to form at least two layers. The materials included in the laminate may comprise single layer materials or laminates of similar or different materials. Further, any laminates comprised in the laminate 220 may have layers that are joined or unjoined with each other.) As shown in FIGS. 5C–5E, a conductive member 205 may also be disposed between the first distal portion 210 of the first member 200 and the second member 202. This ensures an acceptable bond between those portions of the diaper 20, may reduce the amount of energy needed to create the bond and may increase the seam's strength and integrity.

Figure 3A:
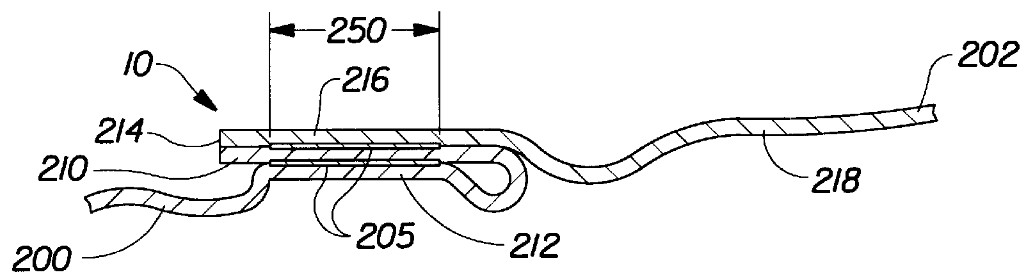
FIG. 3A is an enlarged cross-sectional view of the seam area shown in FIG. 3 in an open configuration.

Once the materials comprised in the laminate 220 have been properly configured, the seam 10 is formed. The seam 10 comprises those portions of the laminate 220 that are joined together (i.e. at least a portion of the first member 200 and at least a portion of the second member 202). To form the seam 10, an electromagnetic field is applied across at least a portion of the laminate 220. In one preferred embodiment, the electromagnetic field is applied across the seam area 250 as shown in FIG. 3. The electromagnetic field heats the conductive member(s) 205 to a temperature which melts and joins at least a portion of the first member 200 and at least a portion of the second member 202. (As described above, in alternative embodiments, the conductive member (s) 205 may heat a material such as a hot melt adhesive or cohesive located in the seam area 250 which acts to join at least a portion of the first member 200 and a portion of the second member 202.) Preferably, at least the first distal portion 210 of the first member 200 is joined to the first proximal portion 212 and the second distal portion 216. Preferably, at least a portion of the second proximal portion 218 remains unjoined from the second distal portion 216. Thus, a flangeless seam 10 is formed that may be "opened" to the relatively planar configuration shown in FIG. 3A. (As used herein, the terms "open" or "opened" refer to pulling apart or separating predetermined portions of the laminate 220, such as the second proximal portion 218 and the second distal portion 216, once the laminate has been seamed so as to form a relatively planar configuration, an example of which is shown in FIG. 3A.)

Figure 9:
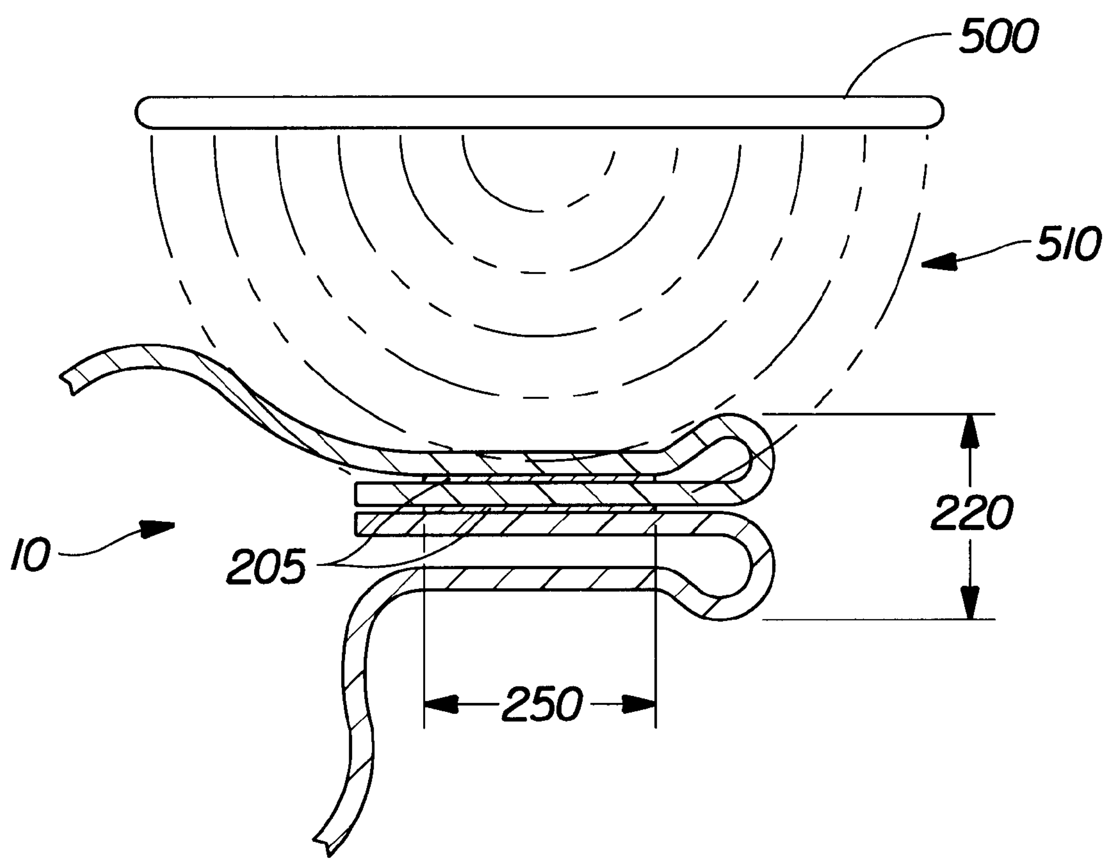
FIG. 9 is a cross-sectional view of one embodiment of the apparatus used to make the seam of the present invention.

The electromagnetic field used to heat the conductive member 205 may be provided by any means known in the art. In one embodiment, as shown in FIG. 9, the electromagnetic field 510 is provided by an induction coil 500. (An exemplary induction coil is the Nova Series induction heating power supply available from Ameritherm, Inc. of Scottsville, N.Y. Specifically, a NOVA3, 3Kw power supply (220 volts, 60 Hz, 3 phase) powering a small pancake style induction coil operating at 393 Khz has been found to be suitable.) The induction coil 500 is placed in the proximity of the seaming area 250 such that the electromagnetic field 510 produced by the coil radiates across the conductive members 205. While not wishing to be limited by theory, it is believed that the primary mechanism for heating the conductive member 205 is Joule heating resulting from the decay of a current which is induced in the conductive member 205 by the external electromagnetic field 510. A secondary heating mechanism is found when magnetic conductive members 205 are used. The additional heating occurs due to an hysteric loss in the material at temperatures below the Curie temperature of the material. In either case, the conductive member 205 is heated to a temperature at which the conductive member 205 transfers enough heat energy to the surrounding materials to melt or activate the materials, thus, joining them.

The method of the present invention may also include the step of applying a secondary joining means across the seam area 250. Such secondary joining means may be used to increase the seam strength or to otherwise modify the characteristics of the seam 10. The joining means may comprise any means suitable for joining the materials comprised in the first and second members 200 and 202. However, a joining means must be chosen that will join the desired portion or portions of the first member 200 with the desired portion or portions of the second member 202 while not joining to those portions of the first member 200 and the second member 202 which have been designated to remain unjoined. Suitable joining means include, but are not limited to, adhesives, pressure bonding means, heat bonding means, heat and pressure bonding means, ultrasound bonding means, infrared bonding means or any other joining means or combination of joining means known in the art.

Examples of suitable adhesive joining means include, but are not limited to, hot melt adhesives such as Ato Findley H-2120, or Ato Findley H-2379 available from Ato Findley Adhesives Corporation of Wauwatosa, Wis. Such adhesive may be applied with slot, spiral or control spray coating equipment such as those available from Nordson Corporation of Norcross, Ga. Examples of methods and apparatus for treating materials with ultrasonic energy are disclosed in U.S. Pat. No. 3,657,033 issued to Sager on Apr. 18, 1972 entitled "Method and Apparatus for Continuous Cutting and Joining of Thermoplastic Sheet Material"; U.S. Pat. No. 4,400,227 issued to Riemersma on Aug. 23, 1983; U.S. Pat. No. 4,430,148 issued to Schaefer on Feb. 7, 1984; U.S. Pat. No. 4,560,427 issued to Flood on Dec. 24, 1985 entitled "Ultrasonic Seal and Cut Method and Apparatus"; and U.S. Pat. No. 4,693,771 issued to Payet, et al. on Sep. 15, 1987 entitled "Woven Textile Fabric Having and Ultrasonically Cut and Sealed Edge and Apparatus and Process for Producing Same"; all of which references are incorporated herein by reference. U.S. Pat. No. 5,236,430 entitled "Disposable Training Pant Having Fusion-Slit Side Seams", issued to Russell Bridges on Aug. 17, 1993; and U.S. Pat. No. 3,457,132 issued to Tuma, et al. on Jul. 22, 1969 entitled "Apparatus for Severing and Sealing Webs of Heat Sealable Packaging Material in a Single Operation", disclose preferred methods and apparatus for severing and sealing webs using thermal energy and mechanical energy including ultrasound. These references are also incorporated herein by reference.

The method of the present invention may also include the step of providing a barrier member 300, as shown in FIGS. 6–8. The barrier member 300 is provided to ensure that when the seam 10 is formed, joining the first member 200 and the second member 202, at least a portion of the first member 200 is not joined with at least a portion of the second member 202. The barrier member 300 may take on any shape, size or configuration suitable for the particular seam to be formed. The barrier member 300 may comprise a single layer or any number of layers. (The multi-layer configurations may comprise a single barrier member folded upon itself any number of times or may comprise layers of unjoined material) The barrier member 300 may comprise any known material or means that will prevent the first member 200 and the second member 202 from becoming fully joined when the seam is formed. Further, the barrier member 300 may be a separate element joined to the first member or a separate member not joined to the first member 200, but merely provided in a position to act as a barrier while the seam is being formed. Alternatively, the barrier member 300 may comprise an element or material that is unitary or integrated with at least a portion of the first member 200, such as a material coextruded with the first member 200, or portion of the first member that has been chemically, mechanically or otherwise manipulated to act as a barrier to the joining means used to form the seam 10. In one embodiment, the barrier member 300 may comprise the conductive member 205. For example, the conductive member may provide heat to form the seam 10 but may not become part of the seam 10. In such cases, the conductive member may be removed when the seam is opened to a flangeless configuration.

Examples of suitable barrier members include, but are not limited to KEVLAR, NYLON, polypropylene films, polyethylene films, scrims, woven materials or laminates of any these or any other suitable materials known in the art. Other suitable barrier member materials may comprise silicone, talc, clay, TEFLON, lotions or any other suitable release means that will prevent predetermined portions of the barrier member 205 from becoming joined when the joining means 300 is applied. Yet other suitable barrier members comprise foams; laminates of films, foams and/or nonwoven webs; adhesives; coated or non-coated paper products such as paper towels or tissue; cotton and cotton-flocked films. Generally, the composition of the barrier member 205 will be limited only by the particular joining means 300 which will be used and the strength characteristics necessary to provide an acceptable seam.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a flangeless seam by joining two members of a disposable article, the method comprising the steps of:
- providing a first member of the disposable article;
- folding the first member of the disposable article providing opposing first proximal and first distal portions of the first member;
- providing a conductive member adjacent at least a portion of the first member;
- providing a second member of the disposable article juxtaposed at least a portion of the first member to form a laminate including the first member, the second member and the conductive member; and
- applying an electromagnetic field across at least a portion of the laminate to heat the conductive member to a temperature which joins at least a portion of the first member and at least a portion of the second member.

2. The method of claim 1 wherein the conductive member is integral with at least a portion of the second member.

3. The method of claim 1 wherein the first member is folded about both the conductive member and at least a portion of the second member.

4. A method of making a flangeless seam by joining two members of a disposable article, the method comprising the steps of:
- providing a first member of the disposable article;
- providing a conductive member adjacent at least a portion of the first member;
- folding the first member of the disposable article about the conductive member providing opposing first proximal and first distal portions of the first member, the conductive member being disposed at least partially between the opposing first proximal and first distal portions;

providing a second member of the disposable article in a folded configuration juxtaposed at least a portion of the first member to form a laminate including the first member and the second member; and applying an electromagnetic field across at least a portion of the laminate to heat the conductive member to a temperature which joins at least a portion of the first member and at least a portion of the second member.

5. The method of claim 4 further comprising the step of pulling apart the first member and the second member to form a flangeless seam.

6. The method of claim 4 further comprising the step of removing the conductive member after the first member and the second member have been joined.

7. The method of claim 4 wherein the step of folding the first member includes folding the first member before the conductive member is interposed between the opposing first proximal and first distal portions.

8. The method of claim 4 wherein the first member includes more than one fold.

9. The method of claim 4 wherein the conductive member is integral with at least a portion of the first member.

10. The method of claim 4 wherein the first member is folded about both the conductive member and at least a portion of the second member.

11. The method of claim 4 wherein the conductive member includes a material selected from the following group: metallic foil, metallic screen or metallic powder.

12. A method of making a flangeless seam by joining two members of a disposable article, the method comprising the steps of:

providing a first member of the disposable article;

folding the first member of the disposable article providing opposing first proximal and first distal portions of the first member;

providing a heat activatable adhesive adjacent at least a portion of the first distal portion;

providing a conductive member adjacent at least a portion of the first distal portion;

providing a second member of the disposable article juxtaposed at least a portion of the first member to form a laminate including the first member, the second member, the heat activatable adhesive and the conductive member; and applying an electromagnetic field across at least a portion of the laminate to heat the conductive member to a temperature which activates the heat activatable adhesive such that the adhesive joins at least a portion of the first member and at least a portion of the second member.

13. A method of making a flangeless seam by joining two members of a disposable article, the method comprising the steps of:

providing a first member of the disposable article;

providing a conductive member adjacent at least a portion of the first member;

folding the first member of the disposable article about the conductive member providing opposing first proximal and first distal portions of the first member, the conductive member being disposed at least partially between the opposing first proximal and first distal portions;

providing a second member of the disposable article in a folded configuration having a second proximal portion and a second distal portion, the second distal portion being juxtaposed at least a portion of the first member to form a laminate including the first member, the second member and the conductive member;

providing an electromagnetic field across at least a portion of the laminate to heat the conductive member to a temperature which joins at least a portion of the first distal portion, the second distal portion and the second proximal portion, the conductive member also preventing the joining of the first proximal portion with the first distal portion;

removing the conductive means; and pulling apart the first proximal portion and the first distal portion to form a flangeless seam.

14. The method of claim 13 further including providing a secondary joining means across at least a portion of the laminate.

15. The method of claim 14 wherein the secondary joining means includes an adhesive.

16. The method of claim 14 wherein the barrier member prevents the secondary joining means from joining the first proximal portion with the first distal portion.

17. A method of making a flangeless seam by joining two members of a disposable article, the method comprising the steps of:

providing a first member of the disposable article;

providing a conductive member adjacent at least a portion of the first member;

folding the first member of the disposable article about the conductive member providing opposing first proximal and first distal portions of the first member, the barrier member being disposed at least partially between the opposing first proximal and first distal portions;

providing a second member of the disposable article in a folded configuration defining opposing second proximal and second distal portions, at least a portion of the second distal portion being juxtaposed at least a portion of the first member to form a laminate including the first member, the second member and the conductive member;

providing a barrier member between the second proximal portion and the second distal portion;

providing an electromagnetic field means across at least a portion of the laminate to heat the conductive member to a temperature which joins at least a portion of the first member and the second member, the conductive member preventing the joining means from joining the second proximal portion with the second distal portion;

removing the barrier member; and pulling apart the second proximal portion and the second distal portion to form a flangeless seam.

18. The method of claim 17 further including providing a secondary joining means across at least a portion of the laminate.

19. The method of claim 18 wherein the secondary joining means includes an adhesive.

20. The method of claim 17 wherein the barrier member prevents the secondary joining means from joining the first proximal portion with the first distal portion.

* * * * *